United States Patent [19]

Ogata et al.

[11] 4,301,159
[45] Nov. 17, 1981

[54] N-(DIETHYLAMINOETHYL)-2-ALKOXY-BENZAMIDE DERIVATIVES

[75] Inventors: Masaru Ogata, Kobe; Hiroshi Matsumoto, Ibaraki; Katsumi Hirose, Kishiwada; Masami Eigyo, Kawanishi, all of Japan

[73] Assignee: Shionogi & Co., Ltd., Osaka, Japan

[21] Appl. No.: 161,492

[22] Filed: Jun. 20, 1980

[51] Int. Cl.$^3$ .................. C07C 143/74; A61K 31/25
[52] U.S. Cl. .................. 424/230; 424/321; 424/324; 564/77; 564/99; 564/167; 564/169
[58] Field of Search .............. 564/79, 99, 167, 169; 424/321, 324, 230

[56] References Cited

U.S. PATENT DOCUMENTS

| | | | |
|---|---|---|---|
| 2,691,025 | 10/1954 | Clinton et al. | 564/167 X |
| 3,177,252 | 4/1965 | Thominet | 564/167 |
| 3,219,528 | 11/1965 | Thominet | 564/167 X |
| 3,357,978 | 12/1967 | Thominet | 564/167 X |
| 3,591,634 | 7/1971 | Thominet | 564/167 X |
| 3,700,719 | 10/1972 | Murakami et al. | 564/167 X |
| 3,739,030 | 6/1973 | Gradnik et al. | 564/167 |
| 3,892,802 | 7/1975 | Podesva et al. | 564/167 X |

*Primary Examiner*—Arthur P. Demers
*Attorney, Agent, or Firm*—Birch, Stewart, Kolasch & Birch

[57] ABSTRACT

A compound of the formula:

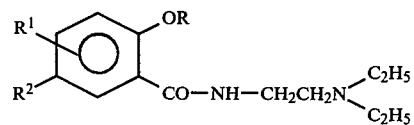

wherein
R is alkyl;
$R^1$ is hydrogen, halogen, alkyl or alkoxy;
$R^2$ is amino, alkanoyl, $$\text{or } R^4\!-\!\overset{|}{N}\!-\!SO_2R^3;$$

$R^3$ is alkyl or dialkylamino; and
$R^4$ is hydrogen or alkyl
with the proviso that when $R^2$ is amino or alkanoyl, $R^1$ is alkyl
and or a pharmaceutically acceptable acid addition salt thereof, being useful as gastric disorder remedies or antiemetics are provided via several routes.

5 Claims, No Drawings

N-(DIETHYLAMINOETHYL)-2-ALKOXY-BENZAMIDE DERIVATIVES

BACKGROUND OF THE INVENTION

The present invention relates to N-(diethylaminoethyl)-2-alkoxybenzamide derivatives which are useful as gastric disorder remedies or antiemetics. More particularly, this invention relates to a compound of the formula:

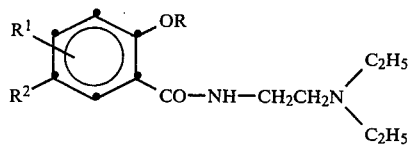

wherein
R is $C_1$–$C_5$ alkyl;
$R^1$ is hydrogen, halogen, $C_1$–$C_5$ alkyl, or $C_1$–$C_5$ alkoxy;
$R^2$ is amino, $C_1$–$C_5$ alkanoyl, or

$R^3$ is $C_1$–$C_5$ alkyl or $C_2$–$C_{10}$ dialkylamino; and
$R^4$ is hydrogen or $C_1$–$C_5$ alkyl;
with the provision that when $R^2$ is amino or $C_1$–$C_5$ alkanoyl, $R^1$ is $C_1$–$C_5$ alkyl
or a pharmaceutically acceptable acid addition salt thereof.

This type of compounds are disclosed in U.S. Pat. No. 3,177,252 and particularly metoclopramide being commercially available has a disadvantage of rather strong toxicity.

DESCRIPTION OF THE INVENTION

As the result of various investigations for the purpose of overcoming the problem of toxicity of metoclopramide, the present inventors have found that said compound (I) shows excellent pharmacological activities such as gastric emptying activity and antiemesis with rather lower toxicity.

In the above formula (I) the definition of the terms herein used is explained illustratively as follows:
alkyl means methyl, ethyl, propyl, isopropyl, butyl, isobutyl, sec-butyl, t-butyl, pentyl, isopentyl, etc.;
alkoxy means methoxy, ethoxy, propoxy, isopropoxy, butoxy, isobutoxy, pentyloxy, etc.;
alkanoyl means formyl, acetyl, propionyl, butyryl, isobutyryl, valeryl, isovaleryl etc.;
dialkylamino means dimethylamino, diethylamino, dipropylamino, dibutylamino, methylethylamino, methylpropylamino etc.; and
halogen means chlorine, bromine, iodine, fluorine, etc.

The compound (I) of this invention can be prepared according to the following scheme:
Route I

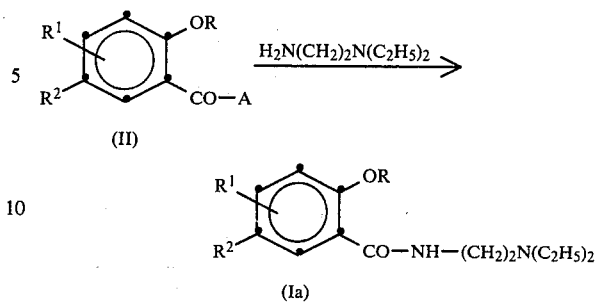

(wherein A is hydroxy, alkoxy, alkoxycarbonyl, or halogen).

The reaction is performed in an inert solvent (e.g. acetone, dimethylformamide, methanol, benzene, dimethylsulfoxide, methylene chloride) at room temperature or under heating up to the boiling point of the solvent used, if necessary, in the presence of a condensing agent (e.g. DDC) and a base (e.g. triethylamine, pyridine).

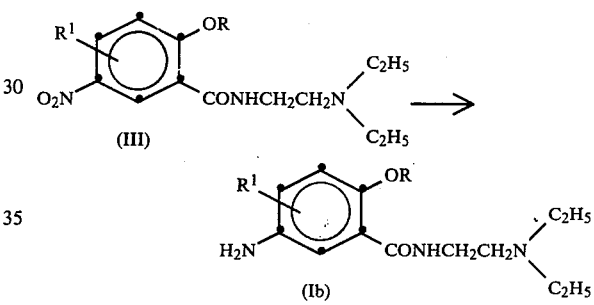

The reduction is performed with a reducing means selected from hydrogenation over a catalyst (e.g. palladium carbon, platinum oxide, Raney nickel) and tin dust—or iron dust—hydrochloric acid in an inert solvent (e.g. methanol, ethanol, tetrahydrofuran, methylene chloride) at room temperature or under heating up to the boiling point of the solvent used. The starting compound (III) is prepared by reacting the corresponding benzoyl chloride with N,N-di-ethylethylenediamine in the presence of a base (e.g. triethylamine);

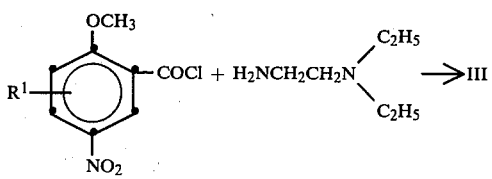

Route III

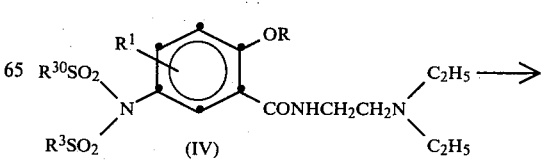

-continued

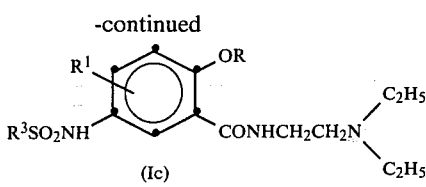
(Ic)

(wherein $R^{30}$ is alkyl).

The hydrolysis is carried out by treating with an alkali hydroxide (e.g. sodium hydroxide, potassium hydroxide) in a suitable solvent (e.g. methanol, ethanol, acetone, dimethysulfoxide) at room temperature or under heating up to the boiling point of the solvent used.

Alternatively Compound (Ic) is directly prepared by reacting Compound (Ib) with a sulfonating agent of the formula:

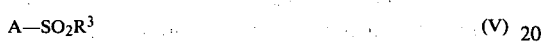

(wherein A is halogen) in the presence of a base (e.g. pyridine) in an inert solvent (e.g. methylene chloride, benzene, toluene, dioxane, tetrahydrofuran, dimethylsulfoxide, dimethylformamide) at room temperature or under heating up to the boiling point of the solvent used.

The starting compound (IV) is prepared by reacting Compound (Ib) with 2 mol of the sulfonating agent (V) in the presence of triethylamine or with 2 different sorts of the sulfonating agent stepwise.

Route IV

Compound Id ($R^4$=alkyl for I) is, if desired, is prepared by reacting Compound (Ic)

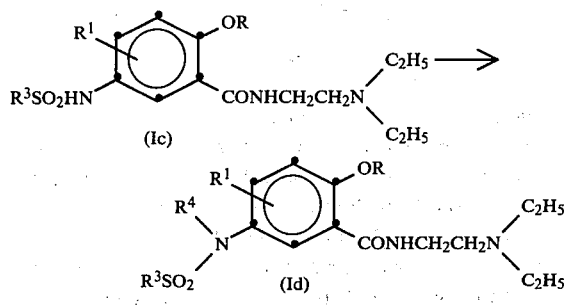

with an alkylating agent (e.g. alkyl halide, dialkyl sulfate) in the presence of a base (e.g. potassium carbonate, triethylamine, pyridine) in an inert solvent (e.g. dimethylformamide, tetrahydrofuran, dioxane, benzene, toluene) at room temperature or under heating up to the boiling point of the solvent used.

Thus obtained Compound (I) can be converted into the acid addition salts thereof for the purpose of formulation, crystallization, and stabilization. Such acids to form those salts include inorganic acids (e.g. hydrochloric acid, hydrobromic acid, sulfuric acid, nitric acid, phosphoric acid) and organic acids (e.g. succinic acid, citric acid, maleic acid, methanesulfonic acid, acetic acid).

Compound (I) and pharmaceutically acid addition salts thereof are useful as gastric disorder remedies or antiemetics, showing excellent gastrointestinal motility stimulation, gastric emptying activity, and antiemesis. For example, N-(diethylaminoethyl)-5-amino-2-methoxy-3-methylbenzamide showed gastric emptying activity (49.2%) almost equal to metoclopramide, and N-(diethylaminoethyl)- 2-methoxy-4-chloro-5-methanesulfonamidobenzamide showed antiemesis ($ED_{50}$=0.5 mg/kg) in dogs comparable to metoclopramide with more than 4 times less acute toxicity ($LD_{50}$=1000 g/kg) in mice (p.o.) than the latter. Other compounds of this invention showed similar pharmacological activities.

Note:
(a) Gastric emptying activity in mice:
Gastric emptying ratio was assessed by a modified method of Jacoby & Brodie (G. I. Jacoby, D. A. Brodie: Gastroenterology, 52, 676, 1967), using each group of ten SLC-ddY male mice which were deprived of food for 24 hours prior to the experiments, with water ad lib. Twenty minutes after oral administration of a test compound, 0.15 ml of silver powder suspension (silver powder 60%; arabic gum 40%) was given into the stomach of mice. Three minutes later, silver powder remaining in the stomach of mice killed was recovered on a filter paper and weighed after drying. Result was shown as percent to that of control in which mice were treated with saline.

(b) Antiemetic activity in dogs:
This test was performed by administering orally a test compound to male beagle dogs of 10 to 20 months age, treating subcutaneously with 0.1 mg/kg of apomorphine one hour later and counting the number of vomitting in 30 minutes. Result was shown by $ED_{50}$(mg/kg) [Janssen, P. A. J. et al., Arzneim.-Forsch. 18 (3) 261–279 (1968)].

(c) Acute toxicity in mice:
Test compounds were orally administered to SLL-ddY male mice with four toxic doses. For each dose 10 mice were used, their body weights ranging from 20 to 23 grams. Test mice were observed for 72 hours after administration. Mortality was calculated with the Bliss method [Bliss: Ann. Appl. Biol., 22, 134–307 (1935); Quant. J. Pharmacol., 11, 192 (1938)].

Compound (I) and pharamceutically acceptable acid addition salts thereof may be applied singly or in combination with pharmaceutical diluents, carriers and/or adjuvants (e.g. water, lactose, wheat starch, corn starch, gelatin, magnesium stearate, talc, vegetable oils, gums, polyalkylene glycol, etc). These can be dispensed in an appropriate formation such as solid form (e.g. tablets, capsules, dragees, gramules, suppositoried) or liquid form (e.g. solutions, suspensions, emulsions) for enteral or parenteral application. Daily dosage of Compound (I) or its salts for oral application to a human adult is about 10 to 400 mg.

EXAMPLE 1

To a solution of N-(diethylaminoethyl)-5-amino 4-chloro-2-methoxybenzamide (1.1 g) and triethylamine (815 mg) in dry methylene chloride (11 ml) is added dropwise a solution of methanesulfonyl chloride (882 mg) in dry methylene chloride (5ml) under ice-cooling and stirring and the resultant mixture is stirred at room temperature for 30 minutes. The reaction mixture is mixed with aqueous sodium hydrogen-carbonate and the methylene chloride layer is separated. The organic layer is washed with water, dried over anhydrous sodium sulfate and concentrated. The intermediary N-(diethylaminoethyl)-5-bis(methanesulfonyl)amino-4-chloro-2-methoxybenzamide obtained as a residue is mixed with 10 % aqueous sodium hydroxide (18ml) and methanol (2 ml) and heated at 50° C. for 30 minutes. The reaction mixture is acidified with conc. hydrochloric acid, neutralized with aqueous sodium hydrogencarbonate, salted out with brine, and shaken with methylene chloride. The organic layer is dried over anhydrous sodium sulfate, and concentrated. The residue is chromatographed on a column of alumina, which is eluted with methylene chloride. The eluate is concentrated and the residue is washed with ethyl acetate - isoproyl ether to give N-(diethylaminoethyl)-4-chloro-5-methanesulfonamido-2-methoxybenzamide (993 mg) as crystals melting at 123° to 123.5° C.

EXAMPLE 2

A solution of N-(diethylaminoethyl)-4-chloro-5-methanesulfonamido-2-methoxybenzamide (570 mg), triethylamine (914 mg) and N,N-dimethylsulfamoyl chloride (1.3 g) in methylene chloride (30 ml) is refluxed for 40 hours. The reaction mixture is mixed with aqueous sodium hydrogen-carbonate. The organic layer is separated, washed with water, dried over anhydrous sodium sulfate and concentrated. The intermediary N-(dimethylaminoethyl)-4-chloro-5-[N-(dimethylaminosulfonyl)-methanesulfonamido]-2-methoxybenzamide obtained as a residue is mixed with 10% aqueous sodium hydroxide (10 ml) and methanol (10 ml) and refluxed for 10 minutes. The reaction mixture is concentrated to remove methanol and the residue is once acidified with 6N hydrochloric acid, neutralized with aqueous sodium hydrogen-carbonate, salted out with brine, and shaken with methylene chloride. The organic layer is dried over anhydrous sodium sulfate and the methylene chloride is evaporated. The residue is chromatographed on a column of alumina, which is eluted with methylene chloride to 1% methanol/methylene chloride. The eluate is concentrated and the residue is washed with ethyl acetate-isopropyl ether to give N-(diethylaminoethyl) -4-chloro-5-(N-dimethylaminosulfonyl)amino-2-methoxybenzamide (410 mg) as crystals melting at 110° to 110.5° C.

EXAMPLES 3–6

Using the subsequent starting material (II), the reaction is carried out as in Example 1, whereby the corresponding product (I) is obtained.

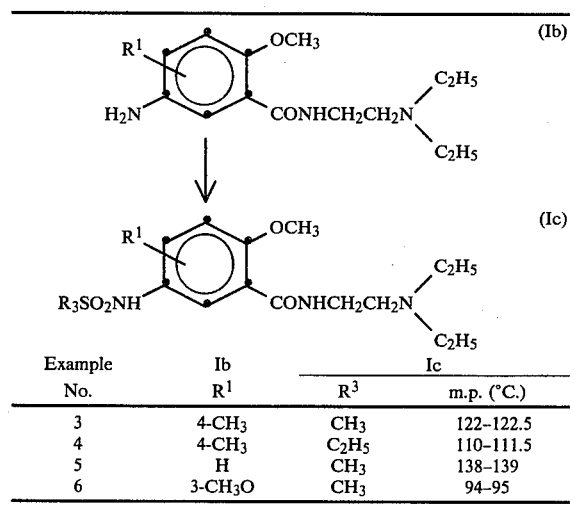

| Example No. | Ib R¹ | R³ | m.p. (°C.) |
|---|---|---|---|
| 3 | 4-CH₃ | CH₃ | 122–122.5 |
| 4 | 4-CH₃ | C₂H₅ | 110–111.5 |
| 5 | H | CH₃ | 138–139 |
| 6 | 3-CH₃O | CH₃ | 94–95 |

EXAMPLE 7

A mixture of N-(diethylaminoethyl)-2-methoxy-3-methyl-5-nitrobenzamide (4.25 g), platinum oxide (425 mg) and methanol (85 ml) is shaken in a hydrogen stream. After absorption of hydrogen stops, the reaction mixture is filtered to remove the catalyst. The filtrate is concentrated under vacuum and the residue is chromatographed on a column of alumina, which is eluated with methylene chloride to methylene chloride-2% methanol. The eluate is concentrated under vacuum and the residue is washed with isopropyl ether to give N-(diethylaminoethyl)-5-amino-2-methoxy-3-methylbenzamide (2.38 g) as crystals melting at 56° to 57° C.

Anal. Calcd. for $C_{15}H_{25}O_2N_3$: C, 64.48; H, 9.02; N, 15.04 (%). Found: C, 64.57; H, 9.13; N, 15.11.

EXAMPLE 8

A mixture of 5-acetyl-2-methoxy-3-methylbenzoic acid (1.0 g), thionyl chloride (1.14 g), and dry benzene (1.14 ml) is refluxed for 30 minutes. The reaction mixture is concentrated under vacuum and the residue is dissolved in acetone (1 ml). N,N-Diethylethylenediamine (558 mg) is added under ice-cooling. The reaction mixture is stirred at room temperature for 15 minutes and concentrated under vacuum. The residue is mixed with icy water, made alkaline with 10% aquenos sodium hydroxide and extracted with methylene chloride. The organic layer is washed with water, dried over anhydrous sodium sulfate and concentrated under vacuum. The residue is chromatographed on a column of alumina, which is eluted with benzene-methylene chloride (1:1), methylene chloride and 1% methanol-methylene chloride in that order. The eluate is concentrated in vacuum to give N-(diethylaminoethyl)-5-acetyl-2-methoxy-3-methylbenzamide (928 mg) as an oil.

Anal. Calcd. for $C_{17}H_{26}O_3N_2.1/5H_2O$: C, 65.86; H, 8.58; N, 9.04. Found: C, 65.47; H, 8.73; N, 8.90.

IR: $\nu^{film}$ 3350 (NH), 1683, 1658 (CO) cm$^{-1}$.

EXAMPLES 9–20

Using the starting material (II), the reaction is performed as in Example 8, whereby the corresponding product (Ia) is prepared.

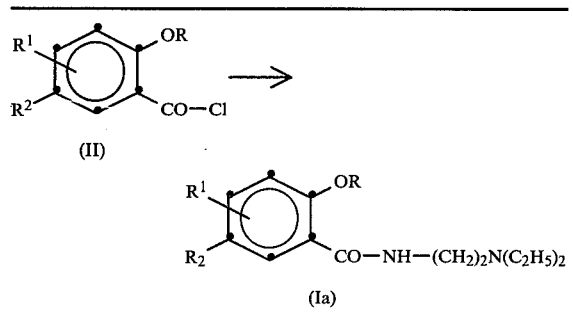

| Ex. No. | R | R¹ | R² | mp (°C.) or IR (cm⁻¹) |
|---|---|---|---|---|
| 9 | C₂H₅ | 3-CH₃ | CH₃CO— | 3360, 1683, 1655 (film) |
| 10 | CH₃ | " | C₂H₅—CO— | 3350, 1683, 1658 (film) |
| 11 | " | " | CH₃SO₂NH— | 147–148 |
| 12 | " | " | C₂H₅—SO₂NH— | 111–112 |
| 13 | " | " | Pr—SO₂NH— | 120.5–122 |
| 14 | " | " | C₂H₅—SO₂NH— | 119.5–121 |

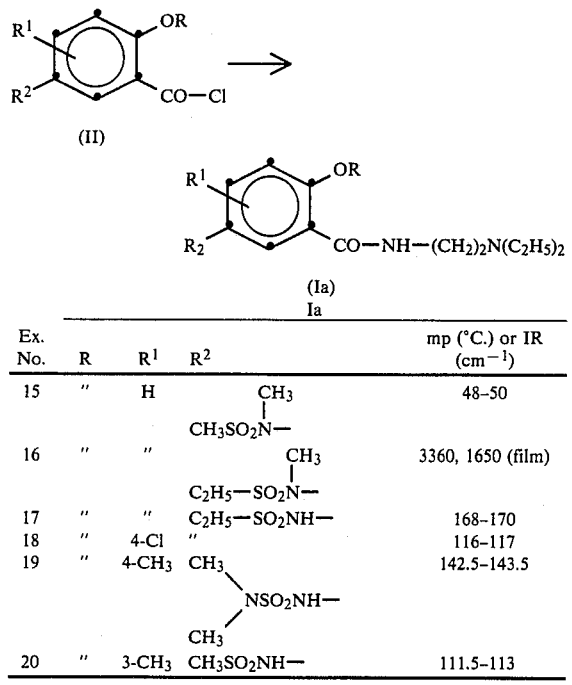

| Ex. No. | R | R¹ | R² | mp (°C.) or IR (cm$^{-1}$) |
| --- | --- | --- | --- | --- |
| 15 | " | H | CH$_3$SO$_2$N(CH$_3$)— | 48–50 |
| 16 | " | " | C$_2$H$_5$—SO$_2$N(CH$_3$)— | 3360, 1650 (film) |
| 17 | " | " | C$_2$H$_5$—SO$_2$NH— | 168–170 |
| 18 | " | 4-Cl | " | 116–117 |
| 19 | " | 4-CH$_3$ | (CH$_3$)$_2$NSO$_2$NH— | 142.5–143.5 |
| 20 | " | 3-CH$_3$ | CH$_3$SO$_2$NH— | 111.5–113 |

Note:
Above symbol has the following significance. Pr (propyl)

EXAMPLE 21

To a solution of N-(diethylaminoethyl)-5-methanesulfonamido-2-methoxybenzamide in acetone are added dimethyl sulfate and potassium carbonate. The resultant mixture is refluxed for 2 hours. After evaporating the solvent, the residue is mixed with water and shaken with methylene chloride. The organic layer is washed with water, dried over anhydrous sodium sulfate, and concentrated in vacuum. The residue is washed with isopropyl ether to give N-(diethylaminoethyl)-2-methoxy-5-(N-methyl-methanesulfonamido)benzamide as crystals melting at 48°–50° C.

EXAMPLE 22

Formulation of Tablet:

| | |
| --- | --- |
| N-(Diethylaminoethyl)-5-acetyl-2-methoxy-3-methylbenzamide | 60 mg |
| Lactose | 250 mg |
| Wheat starch | 80 mg |
| Magnesium stearate | 10 mg |
| | 400 mg |

What we claim is:

1. A compound of the formula:

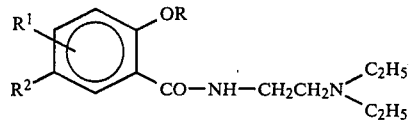

wherein
R is $C_1$–$C_5$ alkyl;
$R^1$ is hydrogen, halogen, $C_1$–$C_5$ alkyl or $C_1$–$C_5$ alkoxy;
$R^2$ is

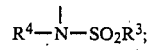

$R^3$ is $C_1$–$C_5$ alkyl or $C_2$–$C_{10}$ dialkylamino, and
$R^4$ is hydrogen or $C_1$–$C_5$ alkyl
or a pharmaceutically acceptable acid addition salt thereof.

2. A compound according to claim 1, namely N-(diethylaminoethyl)-5-ethanesulfonamido-2-methoxy-3-methylbenzamide.

3. A compound according to claim 1, namely N-(diethylaminoethyl)-5-methanesulfonamido-2-methoxy-3-methylbenzamide.

4. A pharmaceutical composition for treating patients suffering from gastric disorders comprising an amount of the compound of claim 1 effective for treating gastric disorders and pharmaceutical carriers, diluents, and/or adjuvants.

5. A method for treating patients suffering from gastric disorders which comprises administering to said patients a pharmaceutical composition of claim 4.

* * * * *